June 13, 1961 C. H. FISCHER Plant Pat. 2,063
GLADIOLUS PLANT
Filed Aug. 23, 1960
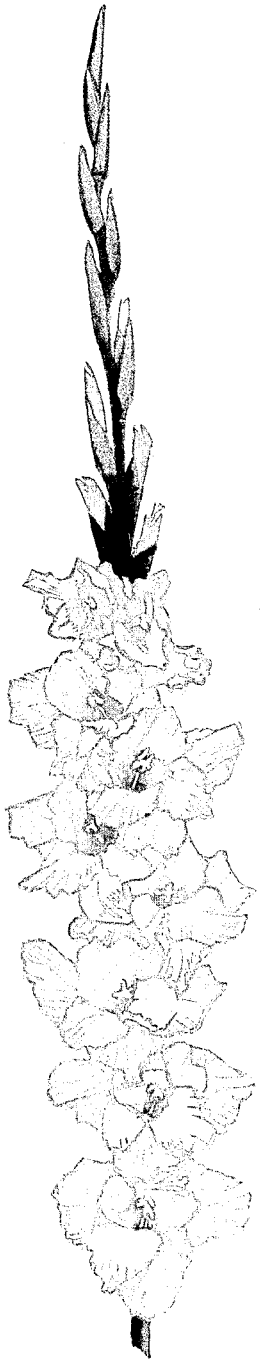
INVENTOR
CARL H. FISCHER
ATTORNEY
Lamont Johnston United States Patent Office Plant Pat. 2,063
Patented June 13, 1961

2,063
GLADIOLUS PLANT

Carl H. Fischer, St. Charles, Minn., assignor to Selected Glads, Inc., New Albany, Ind., a corporation of Tennessee Filed Aug. 23, 1960, Ser. No. 51,477
1 Claim. (Cl. 47—60)

My present invention relates to a new and improved variety of gladiolus plant and is notable particularly for its ruffling, novel combination of orange and yellow coloring and consistent performance.

To the best of my knowledge, this new variety is the result of a cross between an unnamed seedling (unpatented), whose parents were Bonnie Brian and Ophir (both unpatented), and Pactolus (unpatented). The seedling was the seed parent and Pactolus was the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proved to be permanently fixed.

The illustration, made a part of this application, shows a single bloom spike of this new variety, reduced in size, and is as nearly true to color as it is possible to depict. The illustration shows the extreme ruffling, the shape of the florets and the single row arrangement of the florets on the stem. It also shows quite accurately the coloring of orange and yellow.

The color plate references, in the following detailed description, are to the "Horticultural Colour Chart," by The British Colour Council. Where there are other references to color, the ordinary dictionary meanings of the terms are intended.

*The plant*

Growth: Vigorous, averaging 50 to 56 inches in height. Propagates rather slowly.

Blooming: Each spike opens from six to eight 4½-inch flowers at one time. Successive blooms open, totalling an average of eighteen florets to each spike. The variety is a mid-season bloomer, blooming in about 85 days from large bulbs.

Stems: Very straight; stiff. Average diameter at base ½ inch.

Foliage: Deep green and very stiff and upright; average leaf is 1½ inches wide and the plant is 24 to 28 inches high.

Disease resistance: This variety is very resistant to disease. It has been found resistant to Sclerotina Dry Rot, Septoria Leaf Spot and Fusarium Yellows to which some other varieties in my fields have been subject, observed when grown as a seedling under irrigation in a black loam soil in the vicinity of St. Charles, Minnesota, under the natural conditions privided by the climate of that area. At the end of the season, it would be found that many other varities and seedlings had succumbed or been badly affected by the various diseases, whereas this variety remained healthy and unaffected.

Corms: Healthy and plump. They average 2 inches in diameter from adult plants. Husks do not always cover the bulb.

*The flower*

Spike: Tall, slender, has seventeen to eighteen buds and opens two to four florets the first day, following which six to eight are open at one time until all have opened.

Bud:

*Size.*—Opening buds are 2 to 2½ inches long.

*Opening.*—Four to five show color at one time, two to four opening the first day.

Flower:

*Arrangement.*—Flowers are spaced in a single row on the spike and all face in the same direction.

*Size.*—Lower blooms average 4½ inches across when permitted to bloom on the plant in the field. Upper blooms are progressively smaller.

*Form.*—Wide open and ruffled. There is a slight twist to the tips of some of the petals.

*Keeping qualities.*—Keeps and opens well.

Petals:

*Shape.*—Petals are alongated, ruffled and occasionally twisted.

*Size.*—The three upper petals are 1½ to 2 inches in diameter; lower petals are 1 to 1½ inches wide.

*Aspect.*—Substance is heavy; surface is corrugated and ruffled at the edges.

*Fragrance.*—None.

*Color.*—The largest area of the flower is Mandarin Red 17/1, shading to 17/3 on the upper petals. The throat is Primrose Yellow 601/1 and the midribs are Lemon Yellow 4/3.

Reproductive organs:

*Stamens.*—Dresden Yellow 64/3.

*Pistils.*—Three-pronged, extending about the same distances as the stamens. Color is Dresdent Yellow 64/3.

*Comparisons*

My new variety resembles Fire Opan (unpatented) more than any other known variety, but differs from it principally as follows:

(1) My variety is taller than Fire Opal.

(2) My variety has bore of a single row placement of florets.

(3) My variety is more heavily ruffled than Fire Opal.

(4) My variety is smaller in floret size than Fire Opal.

(5) My variety is later maturing than Fire Opal.

(6) My variety has a larger blotch and is more wide open than Fire Opal.

(7) My variety has greater resistance to disease than has Fire Opal.

Having thus disclosed my invention, I claim:

The new and distinct variety of gladiolus plant, substantially as herein shown and described, characterized by its height, intense ruffling and coloring and consistent performance.

No references cited.